(12) United States Patent
Garg et al.

(10) Patent No.: US 6,685,642 B1
(45) Date of Patent: Feb. 3, 2004

(54) SYSTEM AND METHOD FOR BRIGHTENING A CURVE CORRESPONDING TO A SELECTED ULTRASOUND ROI

(75) Inventors: Rohit Garg, Seattle, WA (US); Edward A. Miller, Everett, WA (US); Damien Dolimier, Bothell, WA (US); Danny M. Skyba, Bothell, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/264,066

(22) Filed: Oct. 3, 2002

(51) Int. Cl.$^7$ .................................................. A61B 8/00
(52) U.S. Cl. .................................................... 600/443
(58) Field of Search ................... 600/407–471; 73/620–633; 367/7, 11, 130, 138; 707/1, 10; 345/771, 424, 422, 425; 378/37; 128/904, 916; 355/973, 974

(56) References Cited

U.S. PATENT DOCUMENTS 5,986,662 A * 11/1999 Argiro et al. ............... 345/424

* cited by examiner

Primary Examiner—Ali M. Imam
(74) Attorney, Agent, or Firm—John Vodopia

(57) ABSTRACT

A system and method are provided for simplifying off-line quantification of ultrasound images by displaying a graphical user interface showing a real-time ultrasound image for enabling a user to freeze the real-time ultrasound image to display an image sequence capable of being modified and played back by the user. Upon freezing the real-time image, the graphical user interface displays a tagging system having a corresponding identification tag for each ultrasound image of the image sequence. The graphical user interface further displays time intensity curves each corresponding to an ROI in the frozen image. When the user selects a particular ROI in the frozen image, the curve corresponding to the selected ROI is brightened and the other curves are dimmed.

16 Claims, 3 Drawing Sheets

SYSTEM AND METHOD FOR BRIGHTENING A CURVE CORRESPONDING TO A SELECTED ULTRASOUND ROI

FIELD OF THE INVENTION

The present invention relates generally to ultrasound image quantification and more specifically to a system and method for brightening or highlighting a curve corresponding to a selected region of interest (ROI) figure of an ultrasound image and dimming other curves corresponding to unselected ROI figures during image quantification.

BACKGROUND OF THE INVENTION

Traditionally quantitative analysis of ultrasound image data has been performed on-line, i.e., on the ultrasound system itself. Because of the limitation of performing complex analyses within the clinical workflow, quantification has been limited to two-dimensional x-y data such as areas and lengths, and the analysis of Doppler waveforms. This is due primarily, to limited computational speed of the acquisition/display system and patient workflow management. More recently, complex analysis and measurements have been developed for off-line workstations. Current developments in computational speed are allowing the user to access more complex quantitative analysis both on-line and off-line (e.g. at a PC workstation) in a timely manner. The clinical practice is moving away from just anatomical imaging, to imaging methods which provide functional assessment. This information may be quantitative in nature, which gives the clinician access to physiological data in the management of their patients. These users will require tools to assist them in analyzing this information in a time-efficient and reproducible manner.

Despite the increase in computational power to perform more complex analyses on ultrasound images, there is still the need for user interaction with the ultrasound image data. Ultrasound images are typically stored in movie form, called "CINELOOP™ sequences". Since ultrasound is an inherently real-time imaging modality, CINELOOP™ frame rates are typically in excess of 30 Hz (30 frames/second). Therefore, even a modest 10 second CINELOOP™ image sequence contains over 300 image frames.

Accordingly, there exists a need for enabling a user to interact with the ultrasound image data. Specifically, there exists a need to brighten or highlight a curve corresponding to a selected region of interest (ROI) of an ultrasound image of a CINELOOP™ image and dim any other curves associated with unselected ROI figures.

SUMMARY

An aspect of the present invention is to provide a system and method for brightening or highlighting a curve corresponding to a selected region of interest (ROI) of an ultrasound image of an image sequence and dimming other curves associated with unselected ROI figures.

In a preferred embodiment of the present invention, a system and method are provided for simplifying off-line quantification of ultrasound images by displaying a graphical user interface showing a real-time ultrasound image for enabling a user to freeze the real-time ultrasound image to display an image sequence capable of being modified and played back by the user. Upon freezing the real-time image, the graphical user interface displays a tagging system having a corresponding identification tag for each ultrasound image of the image sequence. When the user selects a particular ROI in the frozen image, the curve corresponding to the selected ROI is brightened and the other curves are dimmed.

The system and method of the present invention are embodied by at least one software module having a series of programmable instructions capable of being executed by a processor for performing its respective functions. The software module includes a series of programmable instructions for enabling a user to select a particular ROI in a frozen ultrasound image and to brighten a curve corresponding to the selected ROI and to dim the curves corresponding to other ROIs.

The software module is preferably stored within a memory storage device, such as a computer hard drive, within a memory module, such as a RAM or ROM module, and/or on a computer readable medium, such as a CD-ROM, and is capable of being accessed for execution by the processor. The software module is preferably incorporated within a software quantification tool for use in off-line image review, quantification and interpretation of ultrasound images and other related data.

BRIEF DESCRIPTION OF THE FIGURES

Various embodiments of the invention will be described herein below with reference to the figures wherein.

DETAILED DESCRIPTION OF THE PREFERRED EMBODIMENTS

Figure 1:
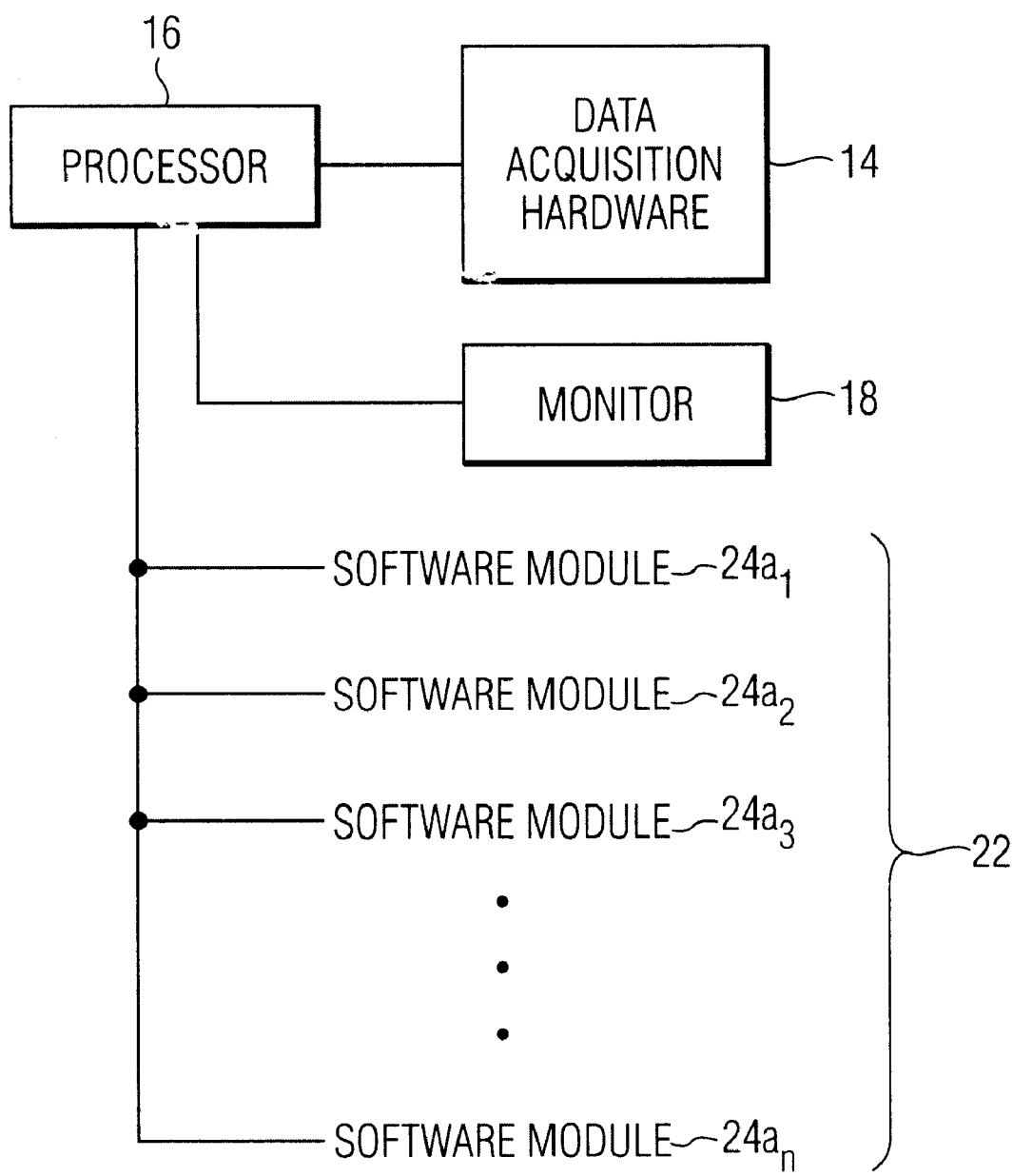
FIG. 1 is a block diagram of the system according to the present invention.

With reference to FIG. 1, there is shown a block diagram of a system according to the present invention and designated generally by reference numeral 10. The system 10 includes an ultrasound imaging system 12, such the SONOS™ 5500 digital echocardiography system or an HDI 5000 system available from Philips Medical Systems, for acquiring and storing ultrasound images. Another embodiment of the system includes an off-line PC workstation capable of reviewing and quantifying the image data acquired on the ultrasound system. The system 12 includes data acquisition hardware 14, such as an ultrasonic transducer and a keyboard, a processor 16 for processing the data, and a monitor 18 capable of displaying a graphical user interface 20 (see FIG. 2) of a software quantification tool. The graphical user interface 20 displays the acquired ultrasound images to a user, as well as other information.

The system 10 further includes operational software 22 capable of being executed by the processor 16 of the ultrasound imaging system 12 for performing the various functions of the imaging system 12, such as ultrasound image acquisition and harmonic image enhancement. The operational software 22 includes a plurality of software modules $24a_1$–$24a_n$ or plug-ins for performing the various functions, including the functions and features of the present invention.

The plurality of software modules $24a_1$–$24a_n$ are preferably stored within a memory storage device, such as a computer hard drive, within a memory module, such as a RAM or ROM module, and/or on a computer readable medium, such as a CD-ROM, and are capable of being accessed for execution by the processor 16. The plurality of software modules $24a_1$–$24a_n$ are preferably incorporated within the software quantification tool for use in off-line image review, quantification and interpretation of ultrasound images and other related data.

Figure 2:
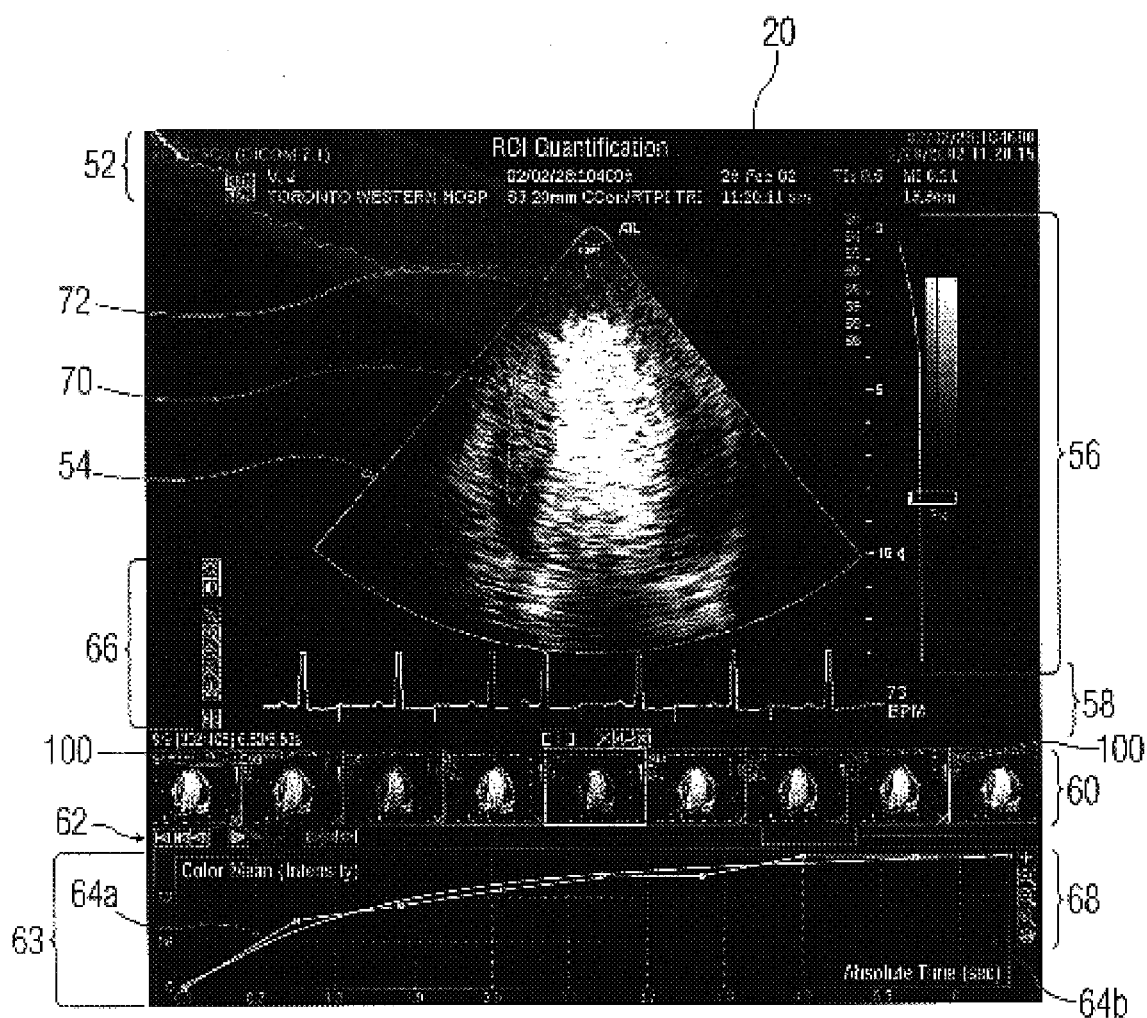
FIG. 2 is a screen view of a graphical user interface capable of being displayed by the system of FIG. 1.

With reference to FIG. 2, there is shown an exemplary screen 50 of the graphical user interface 20. The screen 50 includes time, patient and other data 52 on a top portion, a large frozen or paused playback image 54 of the myocardium, a vertical scale 56 along the right side of the image 54, a bits per minute (BPM) signal 58 below the image 54, a thumbnail representation of the image frames 60, image review control soft buttons 62 (e.g., reverse, forward and play/pause, speed control, jump to first frame, frame step forward, jump to image of interest forward, jump to last frame, frame step backward, jump back to image of interest), a graph 63 displaying time intensity and one minus exponential curves 64a, 64b below the image 54, a first group of soft buttons 66 for at least adjusting the contrast of the image 54, selecting at least one region of interest (ROI) on the image 54, enlarging the image 54, moving the image 54, and zooming in and out with respect to the image 54, and a second group of soft buttons 68 for at least adjusting the position of the graph 63 displaying the curves 64a, 64b, and zooming in and out with respect to the graph 63 displaying the curves 64a, 64b.

In order to obtain the screen 50 of FIG. 2, the user freezes or pauses the large playback image 54 which is being played in real-time by clicking on the image 54 or by some other method. Upon freezing the large playback image 54, the frozen image frame and those preceding and following it are shown in the thumbnail sequence 60, below the frozen image 54, as shown by FIG. 2. The border of the image which corresponds to the large playback image 54 is highlighted in the thumbnail image sequence 60.

Each thumbnail corresponds to a respective image of the image sequence 60 and is tagged by a respective tag of a tagging system. The tagging system primarily includes a plurality of tags 100 or reference numerals identifying each image of the sequence 60. The plurality of tags 100 are embodied within the system 12 as a data structure, such as a top-down stack or a sequence of objects connected by pointers.

Each tag or reference numeral is positioned on the top left portion of each image. The images are tagged or numbered consecutively in the image sequence 60. In the exemplary screen 50, the image of the image sequence 60 identified by numeral 302 corresponds to the large playback image 54.

Two regions of interest 70, 72 are shown on the exemplary screen 50 as defined and selected by the user. The regions of interest 70, 72 are preferably selected by the user using an ROI software module which is preferably one of the plurality of software modules $24a_1$–$24a_n$. The one-minus-exponential curves 64a, 64b are fit by the quantification tool to the ROI data corresponding to the two selected regions of interest 70, 72, respectively.

The system 10 of the present invention includes an ROI bright/dim curve software module $24a_1$ which includes a series of programmable instructions for enabling the user to select a ROI, such as ROIs 70, 72, in the frozen image 54 via a keyboard or other peripheral device, such as a mouse. The time intensity and one-minus-exponential curve for the selected ROI is then brightened or highlighted and the other curves are dimmed. For example, in FIG. 2, the ROI 72 is selected and the curve 64b corresponding to the ROI 72 is brightened, while the other curve corresponding to the ROI 70 is dimmed.

Figure 3A:
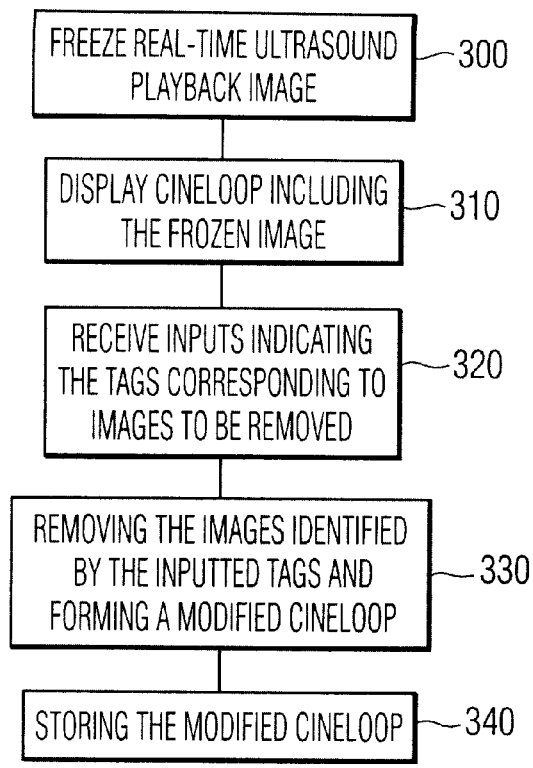
FIG. 3 is an operational flow block diagram illustrating a method of operation according to the present invention.
Figure 3B:
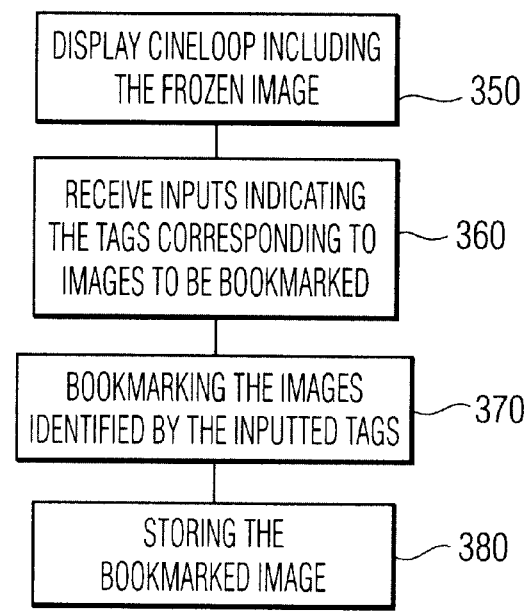

With reference to FIG. 3, there is shown an operational flow block diagram of the method of operation of the ROI bright/dim curve software module $24a_1$ for brightening/dimming curves displayed by the graphical user interface 20 according to the present invention.

With reference to FIG. 3, the system 10, in step 300, accepts an input from a user to freeze a real-time ultrasound image being displayed by the graphical user interface 20 of the ultrasound imaging system 12. In step 310, an image sequence 60 is displayed which includes the frozen image. In step 320, the system 10 receives an input from the user indicating selection of an ROI within the frozen image. In step 330, the curve corresponding to the selected ROI in step 320 is brightened or highlighted and the other curves are dimmed.

Alternatively, the user can select a curve from a plurality of curves by simply clicking on a point on the curve using the mouse and the system 10 brightens the selected curve and dims the non-selected curves from the plurality of curves.

Although the preferred embodiment is related to a system for the review, editing, analysis and storage of ultrasound images, the same tools described above for performing the various functions are relevant to any medical imaging modality that uses real-time data for quantification. Examples of such modalities are X-ray, Computed Tomography, Magnetic Resonance Imaging, and Digital Angiography.

What has been described herein is merely illustrative of the principles of the present invention. For example, the system and method described above and implemented as the best mode for operating the present invention are for illustration purposes only. Other arrangements and methods may be implemented by those skilled in the art without departing from the scope and spirit of this invention.

We claim:

1. A method for processing an ultrasound image comprising the steps of:
    playing a time sequence of ultrasound images in a graphical user interface (GUI) on a display
    receiving at least one input from a user indicating selection of a particular region of interest (ROI) in a single frame of the sequence of ultrasound images, wherein a time intensity curve corresponding to the particular ROI is displayed in said GUI; and
    brightening the time intensity curve corresponding to the particular ROI in the GUI.

2. The method according to claim 1, wherein the GUI displays a plurality of time intensity curves, including said time intensity curve corresponding to the particular ROI, and wherein the method further comprises the step of:
    dimming all of the plural time intensity curves except the brightened time intensity curve.

3. The method according to claim 1, further comprising the steps of:
    receiving an input command from the user to freeze the time sequence of ultrasound images at the single frame, said step being performed prior to the selection of the particular ROI; and
    displaying a plurality of image frames in thumbnail form, wherein the plural thumbnail image frames include a thumbnail of the single frame, and wherein the plural thumbnail image frames form a contiguous series within the time sequence of ultrasound images.

4. A method according to claim 3, wherein the time intensity curve represents an intensity of the particular ROI over a time period of said continuous series of plural thumbnail images.

5. The method according to claim 1, further comprising the step of:
identifying the particular ROI on the ultrasound image.

6. A method for processing an ultrasound image comprising the steps of:
determining either a region of interest (ROI) selected by a user on an ultrasound image displayed in a graphical user interface (GUI) or a time intensity curve selected by the user from a plurality of curves displayed in the GUI, wherein each of the plural time intensity curves corresponds to a ROI;
brightening either a time intensity curve corresponding to the selected region of interest or a ROI corresponding to the selected time intensity curve; and
dimming either all time intensity curves not corresponding to the selected region of interest or all ROIs not corresponding to the selected time intensity curve.

7. The method according to claim 6, further comprising the steps of:
receiving an input command from the user to freeze the time sequence of ultrasound images at the single frame, said step being performed prior to the selection of the particular ROI; and
displaying a plurality of image frames in thumbnail form, wherein the plural thumbnail image frames include a thumbnail of the single frame, and wherein the plural thumbnail image frames form a contiguous series within the time sequence of ultrasound images.

8. The method according to claim 7, wherein the time intensity curves represent intensities of various ROIs over a time period of said contiguous series of plural thumbnail images.

9. An ultrasound imaging system for processing an ultrasound image comprising:
means for playing a time sequence of ultrasound images in a graphical user interface (GUI) on a display;
means for receiving at least one input from a user indicating selection of a particular region of interest (ROI) in a single frame of the sequence of ultrasound images, wherein a time intensity curve corresponding to the particular ROI is displayed in said GUI; and
means for brightening the time intensity curve corresponding to the particular region of interest in the GUI.

10. The system according to claim 9, wherein the GUI displays a plurality of time intensity curves, including said time intensity curve corresponding to the particular ROI, further comprising:
means for dimming all of the plural time intensity curves except the brightened time intensity curve.

11. The system according to claim 9, further comprising:
means for receiving an input command from the user to freeze the time sequence of ultrasound images at the single frame; and
means for displaying a plurality of image frames in thumbnail form, wherein the plural thumbnail image frames include a thumbnail of the single frame, and wherein the plural thumbnail image frames form a contiguous series within the time sequence of ultrasound images.

12. The system according to claim 11, wherein the time intensity curve represents an intensity of the particular ROI over a time period of said contiguous series of plural thumbnail images.

13. The system according to claim 9, further comprising:
means for identifying the particular ROI on the ultrasound image.

14. A data processing method comprising the steps of:
determining either a region of interest (ROI) selected by a user on an image displayed in a graphical user interface (GUI) or a time intensity curve selected by the user from a plurality of time intensity curves;
brightening either a time intensity curve corresponding to the selected ROI or a ROI corresponding to the selected time intensity curve; and
dimming either all time intensity curves not corresponding to the selected ROI or all ROIs not corresponding to the selected time intensity curve.

15. A computer-readable medium storing a serious of programmable instructions for performing a method for processing an ultrasound image, the method comprising the steps of:
playing a time sequence of ultrasound images in a graphical user interface (GUI) on a display;
receiving at least one input from a user indicating selection of a particular region of interest (ROI) in a single frame of the sequence of ultrasound images, wherein a time intensity curve corresponding to the particular ROI is displayed in said GUI; and
brightening the time intensity curve corresponding to the particular (ROI) in the GUI.

16. A computer-readable medium storing a series of programmable instructions for performing a data processing method comprising the steps of:
determining either a region of interest (ROI) selected by a user on an image displayed in a graphical user interface (GUI) or a time intensity curve selected by the user from a plurality of time intensity curves;
brightening either a time intensity curve corresponding to the selected (ROI) or a ROI corresponding to the selected time intensity curve; and
dimming either all time intensity curves not corresponding to the selected (ROI) or all ROIs not corresponding to the selected time intensity curve.

* * * * *